(12) United States Patent
Vrancken Peeters

(10) Patent No.: US 10,085,741 B2
(45) Date of Patent: Oct. 2, 2018

(54) SURGICAL SUTURE APPARATUS

(75) Inventor: Mark-Paul Franciscus Maria Vrancken Peeters, Wassenaar (NL)

(73) Assignee: MELLON MEDICAL B.V., Nijmegen (NL)

( * ) Notice: Subject to any disclaimer, the term of this patent is extended or adjusted under 35 U.S.C. 154(b) by 567 days.

(21) Appl. No.: 14/238,704

(22) PCT Filed: Aug. 30, 2012

(86) PCT No.: PCT/NL2012/050593
§ 371 (c)(1),
(2), (4) Date: May 12, 2014

(87) PCT Pub. No.: WO2013/032329
PCT Pub. Date: Mar. 7, 2013

(65) Prior Publication Data
US 2014/0257345 A1  Sep. 11, 2014

(30) Foreign Application Priority Data

Aug. 30, 2011  (NL) ...................................... 2007318

(51) Int. Cl.
*A61B 17/062* (2006.01)
*A61B 17/04* (2006.01)
(Continued)

(52) U.S. Cl.
CPC ...... *A61B 17/0469* (2013.01); *A61B 17/0625* (2013.01); *A61B 17/2909* (2013.01);
(Continued)

(58) Field of Classification Search
CPC ............ A61B 17/0625; A61B 17/0491; A61B 17/06061; A61B 2017/06019;
(Continued)

(56) References Cited

U.S. PATENT DOCUMENTS 4,602,631 A  7/1986  Funatsu
2011/0130773 A1  6/2011  Saliman et al.

FOREIGN PATENT DOCUMENTS

EP  0764426 A2  3/1997
EP  1300116 A2  4/2003
(Continued)

*Primary Examiner* — Christopher L Templeton
*Assistant Examiner* — George J Ulsh
(74) *Attorney, Agent, or Firm* — Birch, Stewart, Kolasch & Birch, LLP

(57) ABSTRACT

A surgical suture apparatus for open and/or endoscopic surgery is configured to pass a double-ended surgical needle backwards and forwards between a first jaw element and a second jaw element, the jaw elements each including a holding device to hold a respective needle end of the surgical needle, wherein the first and/or second jaw element are biased to an open position with a first biasing force. The apparatus further includes an operating device to operate the first and second holding devices, wherein the operating device includes a first operating organ biased in the normal position by one or more second spring elements with a second biasing force, wherein the first biasing force is smaller than the second biasing force such that exerting an actuation force on the first operating organ first results in movement of the first and second jaw element towards each other, and subsequently in actuation of the operating device.

18 Claims, 8 Drawing Sheets

(51) Int. Cl.
    *A61B 17/06*    (2006.01)
    *A61B 17/29*    (2006.01)
    *A61B 17/30*    (2006.01)

(52) U.S. Cl.
    CPC ......... *A61B 17/0491* (2013.01); *A61B 17/062* (2013.01); *A61B 17/06061* (2013.01); *A61B 2017/0472* (2013.01); *A61B 2017/0609* (2013.01); *A61B 2017/06019* (2013.01); *A61B 2017/06042* (2013.01); *A61B 2017/2936* (2013.01); *A61B 2017/305* (2013.01)

(58) Field of Classification Search
    CPC .. A61B 2017/06042; A61B 2017/0609; A61B 2017/2936; A61B 2017/305; A61B 17/305; A61B 17/0469; A61B 17/2909; A61B 2017/0472; A61B 17/04; A61B 2018/1462; A61B 2017/06014; A61B 17/0482; A61B 17/0486; A61B 2017/0409; A61B 17/29; A61B 17/28; A61B 17/282; A61B 17/0485
    USPC ........................................................ 606/145
    See application file for complete search history.

(56) References Cited

FOREIGN PATENT DOCUMENTS

| | | |
|---|---|---|
| EP | 1304081 A2 | 4/2003 |
| GB | 2260704 A | 4/1993 |

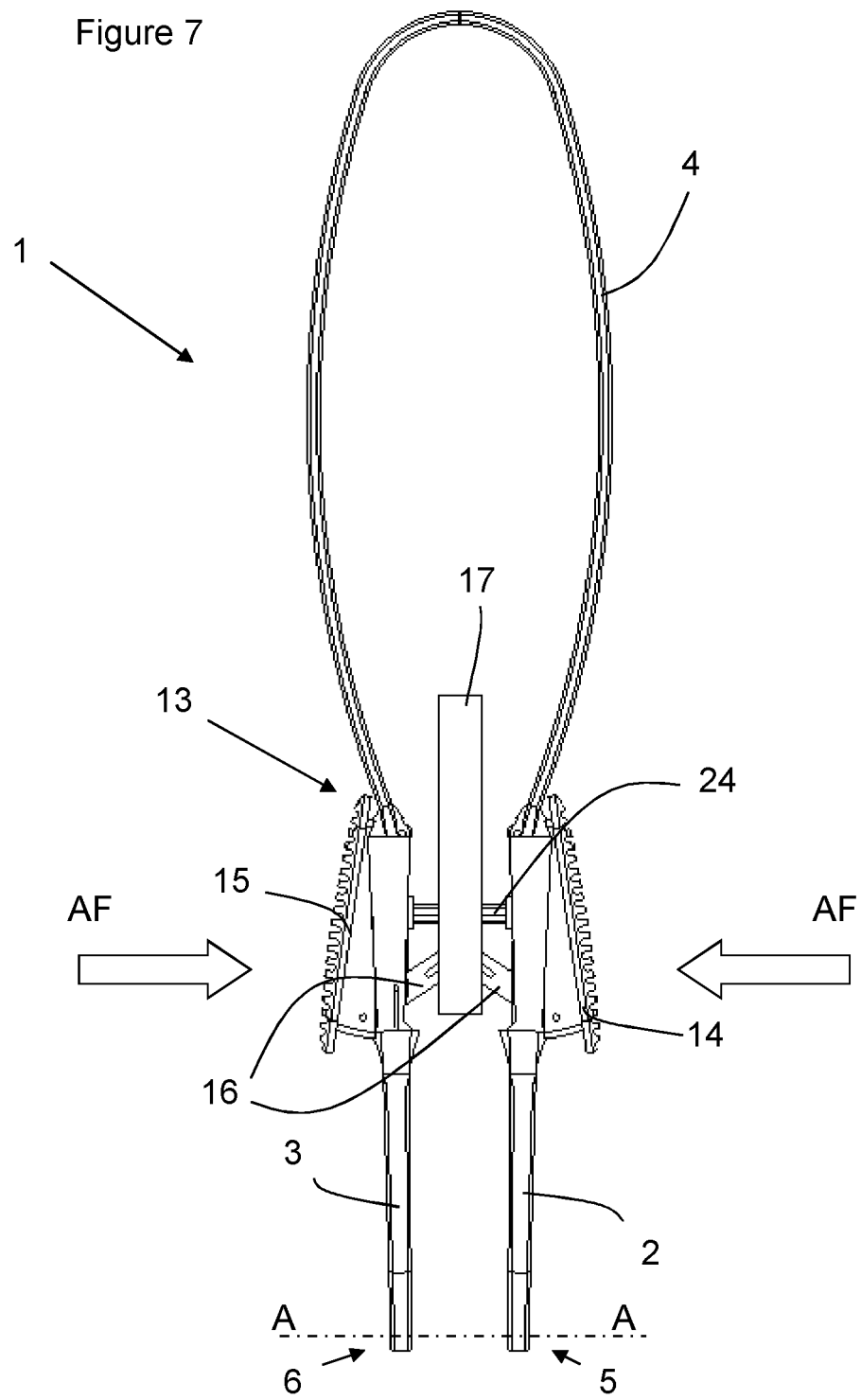

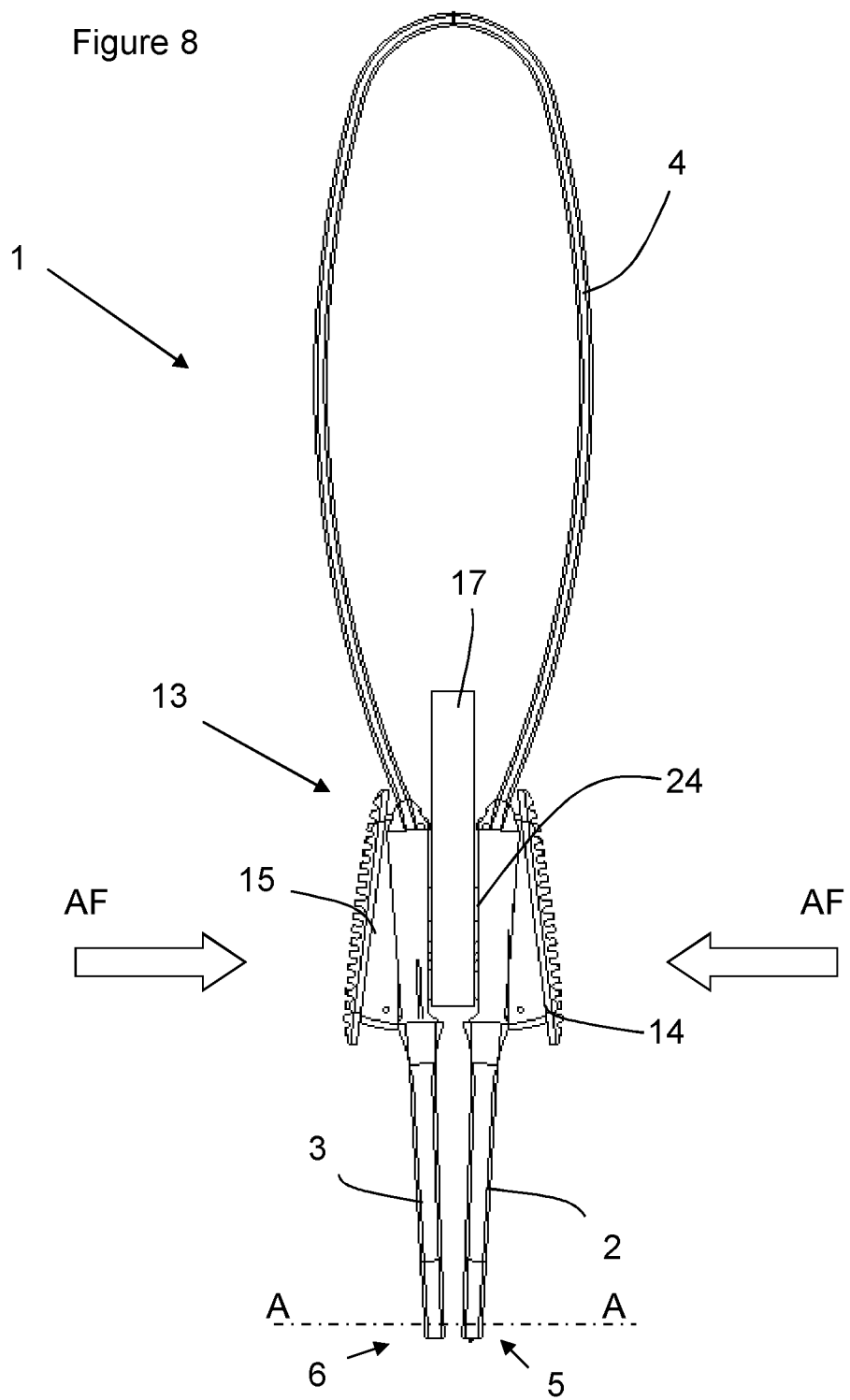

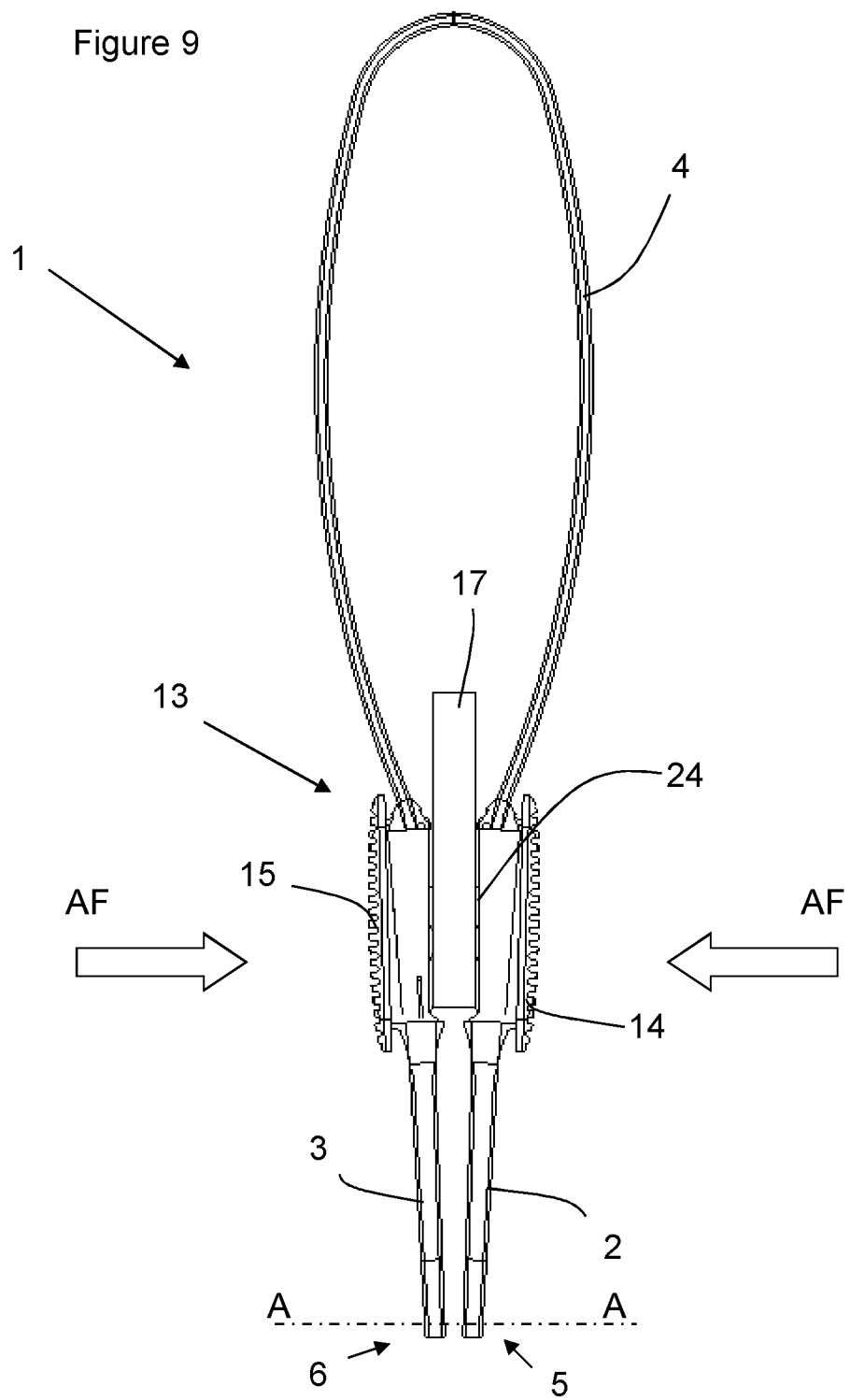

SURGICAL SUTURE APPARATUS

CROSS REFERENCE TO RELATED APPLICATIONS

This application is the National Phase of PCT/NL2012/050593 filed on Aug. 30, 2012, which claims priority under 35 U.S.C. 119(e) to U.S. Provisional Application No. 61/560,994 filed on Nov. 17, 2011, and under 35 U.S.C. 119(a) to Patent Application No. 2007318 filed in the Netherlands on Aug. 30, 2011, all of which are hereby expressly incorporated by reference into the present application.

The present invention relates to a surgical suture apparatus for passing a double-ended surgical needle backwards and forwards.

EP 1 300 116 discloses a surgical suture apparatus for use in laparoscopic surgical procedures.

The surgical apparatus of EP 1 300 116 is configured to pass a surgical needle backwards and forwards between a first and a second jaw element of the apparatus. The surgical apparatus comprises an elongate body portion, the first and second jaw elements extending from a distal end of the body portion, at least one of the jaw elements being movable between an open and closed position. A handle at the proximal end of the body portion is provided to control the jaw elements movements between the open and the closed position.

In each of the jaw elements holding means are provided for holding one end of the surgical needle. A side arm is provided to operate the holding means between two operating positions to alternately hold one end of the surgical needle in a respective jaw element. To this end the side arm is tiltable between two positions. The surgical apparatus is designed such that the side arm can only be actuated, if the jaw elements are brought in the closed position by manipulation of the handle.

A drawback of the surgical apparatus of EP 1 300 116 is that two operating organs are used, i.e. a handle to operate the movement of the at least one movable jaw element and the side arm to activate the holding means to alternately hold the respective needle end in one of the first and second jaw element to operate the apparatus. This makes the operation of the apparatus with a single hand more difficult. In practice, the side arm of the apparatus is often operated by another hand of the user.

GB 2260704 discloses a similar surgical suture apparatus for use in laparoscopic surgical procedures, wherein a surgical needle moves backwards and forwards between a first and a second jaw element of the apparatus. The first jaw element is movable between an open and closed position. This movement is actuated by a stiff actuation cable which is connected to an actuation trigger.

The first and second jaw element each comprise a holding device to alternately hold a needle end of a surgical needle. The holding device is actuated by a second stiff actuation cable which is also connected to the actuation trigger.

A drawback of the surgical apparatus of GB 2260704 is that the use of two stiff actuation cables connected to a single actuation trigger must result in a, non-disclosed, complex operating device vulnerable to malfunctioning of the operation of the device.

Further, drawbacks of the surgical apparatus of EP 1 300 116 and GB 2260704 are that these apparatuses are relatively long and unsuitable for open surgery. Shortening the elongate bodies will decrease the size of the surgical apparatus, but will also worsen the direct view on the surgical needle and the two jaw elements.

EP 0 764 426 discloses a surgical suture apparatus comprising a first jaw element and a second jaw element, the second jaw element being tiltable with respect to the first jaw element between an open position and a take-over position. Each of the first and the second jaw element comprises a needle holding device to hold one end of needle. The suturing apparatus further comprises an operating device to operate the respective holding devices to pass a needle backwards and forwards when the first jaw element and the second jaw element are in the take-over position. The operating device comprises an extension arm on the first jaw. The extension arm carries an actuating lever to actuate the operating device to pass the needle backwards and forwards between the first needle holding device and the second needle holding device.

The suture apparatus of EP 0 764 426 is designed to be held in a single hand and to be squeezed within the hand palm between fingers and the thenar of the hand to move the first jaw element from the open position towards the second jaw element and to subsequently operate the operating device to pass the needle between the needle holding devices. This squeeze operation is not always desirable during surgery procedures.

A further drawback of the prior art devices of EP 1 300 116, GB 2260704 and EP 0 764 426 is that the devices are relatively bulky and comprise a large number of parts. Therefore, the devices may be more vulnerable for defects and less suitable for single use.

It is an aim of the present invention to provide an improved surgical suture apparatus, lacking at least one of the above-mentioned drawbacks.

The present invention provides a surgical suture apparatus for passing a double-ended surgical needle backwards and forwards.

The surgical apparatus comprises a first jaw element and a second jaw element. The first jaw element comprises a first holding device to hold a first needle end of the surgical needle and the second jaw element comprises a second holding device to hold a second needle end of the surgical needle. The first jaw element and second jaw element are movable with respect to each other between a take-over position, wherein a surgical needle can be passed between the first holding device and the second holding device and an open position, wherein the first holding device and second holding device are spaced further from each other. The surgical apparatus comprises one or more first spring elements to bias the first jaw element and the second jaw element to the open position with a first biasing force.

The surgical apparatus further comprises a connecting element connecting the first jaw element and the second jaw element, and an operating device to operate the first holding device and the second holding device to alternately hold the first needle end by the first holding device and the second needle end by the second holding device.

The operating device comprises a first operating organ, wherein the first operating organ is movable between a normal position and a depressed position, the first operating organ being biased to the normal position by one or more second spring elements with a second biasing force. The operating device is actuated by depression and/or subsequent release of the first operating organ.

The first biasing force is smaller than the second biasing force such that exerting an actuation force on the first operating organ first results in movement of the first jaw element and the second jaw element towards each other, and subsequently in actuation of the operating device.

With the apparatus of the invention, a reliable and relatively simple operating device of the surgical apparatus is obtained which uses a single actuation of the operating organ to move the first and second jaw element towards each other and to subsequently operate the first and second holding devices to pass the surgical needle between the first and second jaw elements.

Due to the difference in biasing forces between the first biasing force and the second biasing force, the surgical apparatus can be safely operated by the user, wherein the first and second holding device can only be operated after the first and second jaw element are moved from the open position to the take-over position, also indicated in this patent application as closed position.

It is remarked that the biasing forces are to be determined at the location of the operating organ. The spring forces of the actual springs or other elements providing the biasing forces may differ, for instance as a result of levers in the construction. Furthermore, it is remarked that one or more springs may be arranged in the surgical apparatus which bias both the first operating organ to the normal position and the first jaw element to the open position. Such springs are regarded to be part of the one or more first spring elements and the one or more second spring elements.

Further, it is remarked that although the difference in first and second biasing forces results in reliable operation of the apparatus, a security device may be provided which security device is configured to prevent actuation of the operating device when the first and second jaw element are not in the closed position.

The surgical apparatus may be made of any suitable material, for instance plastics material, and may be configured for single use or multiple uses. Compared to the prior art suture apparatuses, the apparatus of the present invention can be realized with a low number of parts and with a low volume.

The surgical apparatus of the invention can easily be held and operated by a single hand of a user, leaving the other hand free for other tasks.

The first and second holding device are each arranged to hold a needle end. The first and second holding devices which are preferably arranged at or near a distal end of the first and second jaw element, may for example be configured as disclosed in EP 1 300 116, the contents of which are herein incorporated by reference.

In this embodiment each jaw element is provided with a recess which is designed to receive a needle end which needle end is provided with a needle groove. In each jaw element a holding element in the form of a slidable blade is provided which is movable in longitudinal direction of the jaw element between a holding position wherein the blade is partially arranged in the needle groove so that the needle cannot be moved out of the recess, and a free position wherein the slidable blade is not positioned in the needle groove of the needle so that the needle end can be freely moved in and out of the recess.

Any other suitable configuration of a first and second holding device configured to alternately hold the needle end in the first and second jaw element may also be applied. The first and second holding device may be adapted for any type of needle, for example needles without needle grooves at the respective needle ends.

The first jaw element and second jaw element are movable with respect to each other between a take-over position and an open position. In the take-over position the opposite needle ends may for instance be positioned in both the holding devices, for example in the recess of the first holding device and the recess of the second holding device, so that by operating the first holding device and the second holding device the needle can be passed onto the first holding device and the second holding device, respectively.

In the open position the first jaw element and the second jaw element and therewith the first holding device and second holding device are spaced further from each other. The distance between the first holding device and the second holding device will be substantially larger than the length of the surgical needle so that the surgical apparatus can be manipulated to arrange tissue to be sutured between the free needle end, i.e. the needle end that is not held by one of the holding devices and an opposite jaw elements. Then, by further manipulation of the apparatus, the needle can be moved through the tissue at a suitable location at least until the free end of the needle comes out of the tissue. Then, the apparatus can be actuated by an actuation force to move the first and second jaw element to the take-over position and to pass the needle from one of the holding devices to the other holding device so that a suture is provided through the tissue. It is remarked that the first and second jaw elements may also be moved from the open to the take-over position before the needle is pierced through the tissue.

The surgical apparatus of the invention may be used in open surgery and in endoscopic surgery.

The design of the apparatus may be adapted to the specific use. For instance, the length and shape of the jaw elements may be adapted to the location where sutures have to be made. For example, to make sutures located deep within the body, relative long jaw element may be desired, while for microsurgery small and short jaw elements may be more advantageous. The jaw elements may also be hooked to obtain easier access to locations which are difficult to access in a straight line.

In an embodiment, the first operating organ is arranged on the first jaw element at a side faced away from the second jaw element. By arranging the operating organ on this side of the first jaw element, the user will directly manipulate the first jaw element and thus obtain direct feedback of the position of the first jaw element and the force being exerted on the first jaw element. Also, the user has a large flexibility and feeling in manipulating the apparatus in different positions with respect to a patient, since the position and orientation of the hand of the user is directly linked with the position and orientation of the first jaw element.

In an alternative embodiment, for example for endoscopic surgery, the operating organ may be arranged on or integrated in a handle configured to move the first and/or second jaw element. The handle may be directly or indirectly connected to the first and/or second jaw elements for manipulation of the first and/or second jaw elements. Linking elements may be provided between the handle and the first and/or second jaw elements.

The apparatus of the invention may advantageously have the general design of a pair of tweezers. In this design the first operating organ may be arranged on the first jaw element. Pinching actuation forces on the operating organ at one side of the device and the opposite side of the second jaw element will result in a movement of the first and second jaw element towards each other until the take-over position, and subsequently in operating the holding device by actuation of the operating organ. The first and second jaw elements may be hooked for better maneuverability of the location of the first and second holding device which are preferably arranged at or near a distal end of the apparatus.

The first operating organ may for instance be an operating button that is movable between the normal position and the depressed position in a direction substantially equal to the direction of movement of the first jaw element towards the second jaw element.

The pinching actuation force is preferably provided by a pinching force of the thumb and a finger, for instance index and/or middle finger, of a single hand of the user, similar to the operation of a conventional pair of tweezers. By holding the apparatus in this way the apparatus can properly be manipulated by the user, and the user has a good view on at least the distal end of the apparatus. Furthermore, such tweezers grip provides better tactile feedback to the user than a suture apparatus wherein the relative movement of the jaws is obtained by squeezing the jaws within the hand palm between the fingers and the thenar of the hand of the user.

It is remarked that, when desired, the design of the suture apparatus may also allow the user to hold the surgical apparatus within the hand palm, while the actuation force is provided by the thumb and the index and/or middle finger. In some circumstances, for example in endoscopic surgery, such grip may be more advantageous.

In an embodiment, the operating device comprises a second operating organ, for example a second operating button, wherein the second operating organ is movable between a normal position and a depressed position, the second operating organ being biased to the normal position by the one or more second spring elements and/or by one or more third spring elements with a third biasing force, wherein the first biasing force is smaller than the third biasing force.

In such embodiment, the operating device is actuated by depression and/or subsequent release of the first operating organ and the second operating organ.

The second operating organ can be used to have a symmetrical operating construction, wherein the first and second operating organs simultaneously are used to operate the first and second holding device.

In an alternative embodiment, the first operating organ is configured to operate the first holding device and the second operating organ is configured to operate the second holding device.

In an embodiment, the first operating organ is arranged on the first jaw element and the second operating organ is arranged on the second jaw element, wherein the first operating organ and the second operating organ are arranged at opposite sides of the surgical apparatus. Such embodiment has the advantage that the surgical apparatus has a substantially symmetrical construction, wherein the operating organs, for example operating buttons can be simultaneously actuated by exerting a pinching or squeezing actuation force on the operating organs at opposite sides of the surgical apparatus.

Such substantially symmetrical construction can for instance be applied in the above discussed pair-of-tweezers design, wherein the first operating organ can be actuated by a thumb of the user and the second operating organ can be actuated by a finger of the user, or vice versa.

In the tweezers grip a proximal part of the suture apparatus is preferably designed to be supported on the hand or wrist, for example on the web space between the index finger and the thumb and/or on a part of the index finger. This support provides more stability in manipulating of the suture apparatus. This proximal support part of the suture apparatus is preferably formed by the connecting element.

In alternative embodiments, the first and second operating organs may be arranged at opposed sides of two operating handles directly or indirectly connected to the first and/or second jaw element for manipulation of the first and/or second jaw elements. This also provides a symmetric construction for relative movement of the first and second jaw elements and actuation of the operating device. The two operating handles may also be operated in a tweezers grip.

In an embodiment, the operating device comprises a two position switch mechanism, that can be arranged in a first operating position, wherein the first holding device will hold the first needle end, while the second needle end may be moved freely in and out of the second holding device, and a second operating position, wherein the second holding device will hold the second needle end, while the first needle end may be moved freely in and out of the first holding device, and wherein depression and/or subsequent release of the operating organ results in a position change from the first operating position to the second operating position or from the second operating position to the first operating position.

By provision of this two position switch mechanism, the operating device will be positioned in either one of the two operating positions, therewith assuring that the needle will be held by either one of the holding devices.

In an alternative embodiment, a separate operating device may be provided for each of the first holding device and the second holding device. This makes separate control over each of the first and the second holding device possible. In such embodiment a two position switch mechanism may be provided for each of the first and second holding devices.

It is remarked that it may be necessary to configure the apparatus such that the first holding device and/or the second holding device can be manipulated to make positioning of a needle in the apparatus, or releasing a needle from the apparatus possible.

In an embodiment, the connecting element is an arc shaped resilient element connecting a proximal end of the first jaw element to a proximal end of the second jaw element. By providing an arc-shaped element, the first jaw element and the second element can be movably connected to each other without a pivot mechanism, which results in a simple and reliable construction.

Further, the resiliency of the connecting element may be used to bias the first and the second jaw element to the open position. Thus, in such embodiment the one or more first spring elements comprise the connecting element.

Also, the arc-shaped resilient element is suitable to be supported on the web space between the index finger and the thumb and/or a part of the index finger. Such support provides in particular stability when the apparatus is held in the tweezers grip between the thumb and a finger of a single hand. When the apparatus is operated by thumb and index finger, the apparatus may also be supported by the middle finger.

The connecting element may also be supported on any other suitable location on the hand or wrist of the user.

It is remarked that the connecting element may be any device or feature which provides a direct or indirect connection of the first and the second jaw element. For example, in a direct connection by welding the proximal ends of the first jaw element and the second jaw element to each other, the connecting element is formed by the weld.

In an embodiment, the apparatus is designed to move the first holding device and the second holding device over a straight line with respect to each other, when the first jaw element and the second jaw element are moved between the open position and the take-over position. As a consequence, the needle held by one of the first holding device and second holding device moves over a straight line towards the other of the first holding device and the second holding device, when the first jaw element and second jaw element are moved from the open position to the take-over position.

In prior art devices, such as the devices of EP 1 300 116, GB 2260704 and EP 0 764 426, the first jaw element and the second jaw element are rotatably connected to each other, resulting in a relatively rotating movement of the first jaw element and the second jaw element, when being moved from the open position to the take-over position. As a result, the needle held by one of the first holding device and second holding device of such embodiment moves over a circular line towards the other of the first holding device and the second holding device, when the first jaw element and second jaw element are moved from the open position to the take-over position.

The advantage of a straight line movement of the needle is that it results in a reliable and predictable movement of the needle. The position of the needle holding device not holding a needle can be used to more accurately predict where the needle will pierce through the tissue, even when the free needle end is not visible. In a straight line movement of the needle, a straight needle can advantageously be used.

It is remarked that the term straight line, as used in this patent application, also encompasses a substantially straight line. However, a circular line having a radius equal or smaller than a length of the jaw elements of the respective surgical apparatus, is not considered to be a substantially straight line.

Preferably, a substantially straight line, when having a curve, has at least a radius larger than the length of the respective surgical apparatus, more preferably at least 1.5 times the length of the surgical apparatus, even more preferably at least 2 times the length of the surgical apparatus.

In an embodiment, wherein the first holding device and the second holding device move over a straight line with respect to each other, the first and second jaw element, or at least the parts of the first and second jaw element supporting a needle holding device configured to hold a needle, mainly translate with respect to each other during the movement of the first jaw element and the second jaw element between the open position and the take-over position. Some slight rotation of the first jaw element and the second jaw element may occur.

Such mainly translating movement can for instance be obtained by a suitable design of the connecting element connecting the first and second jaw element. The first jaw element and the second jaw element are preferably non-rotatably connected to each other to obtain such mainly translating movement. For example, a resilient element, such as an resilient arc-shaped element may be used as a connecting element, obviating the need of a pivot mechanism rotatably connecting the first jaw element and the second jaw element.

In an embodiment, the surgical apparatus comprises one or more guiding elements configured to guide the first and second jaw element in a mainly translating movement, when the first jaw element and the second jaw element are moved with respect to each other between the open position and the take-over position.

In an embodiment, the apparatus may comprise a guiding device between the first and second jaw element to maintain the first and second jaw element in a substantially parallel position. This guiding device may be formed by the operating device.

Any other device or means, such as a guiding device, to obtain a straight line movement of the first holding device and the second holding device with respect to each other may also be used.

In alternative embodiments, the apparatus may also be designed to rotate the first and second jaw element with respect to each other during a movement between the open position and the take-over position so that the first holding device and the second holding device make a circular movement with respect to each other.

It is remarked that the advantageous straight line movement of the first holding device and the second holding device with respect to each other, when the first jaw element and second jaw element are moved from the open position to the take-over position can also be used in embodiments of a surgical apparatus, in which different actuation forces and/or locations are used for operating the operating device and moving the jaw elements between the open position and the take-over position. The design of such apparatus may further comprise any of the features described in this patent application.

Therefore, the invention also relates to a surgical suture apparatus for passing a double-ended surgical needle backwards and forwards, the surgical apparatus comprising:

a first jaw element and a second jaw element, wherein the first jaw element comprises a first holding device to hold a first needle end of the surgical needle and the second jaw element comprises a second holding device to hold a second needle end of the surgical needle, wherein the first jaw element and second jaw element are movable with respect to each other between a take-over position wherein a surgical needle can be passed between the first holding device and the second holding device and an open position, wherein the first holding device and second holding device are spaced further from each other, wherein the surgical apparatus comprises one or more first spring elements to bias the first jaw element and the second jaw element to the open position with a first biasing force, a connecting element connecting the first jaw element and the second jaw element, and an operating device to operate the first holding device and the second holding device to alternately hold the first needle end by the first holding device and the second needle end by the second holding device, wherein the apparatus is designed to move the first holding device and the second holding device over a straight line with respect to each other, when the first jaw element and the second jaw element are moved between the open position and the take-over position.

In other words, the first and second jaw element, or at least the parts of the first and second jaw element supporting a needle holding device configured to hold a needle mainly translate with respect to each other during the movement of the first jaw element and the second jaw element between the open position and the take-over position.

One or more guiding elements may be provided to guide the first and/or second jaw element in a mainly translating movement, when moved between the open position and the take-over position.

The invention also relates to a method of threading a suture through a tissue section, such as a tubular or layered tissue section of for example vascular, bowel or fascia tissue, comprising the steps of providing a surgical suture apparatus, wherein the suture apparatus comprises:

a first jaw element and a second jaw element, wherein the first jaw element comprises a first holding device to hold a first needle end of the surgical needle and the second jaw element comprises a second holding device to hold a second needle end of the surgical needle, wherein the first jaw element and second jaw element are movable with respect to each other between a take-over position wherein a surgical needle can be passed between the first holding device and the second holding device and an open position, wherein the first holding device and second holding device are spaced further from each other, wherein the surgical apparatus comprises one or more first spring elements to bias the first jaw element and the second jaw element to the open position with a first biasing force, a connecting element connecting the first jaw element and the second jaw element, and an operating device to operate the first holding device and the second holding device to alternately hold the first needle end by the first holding device and the second needle end by the second holding device, piercing the needle held by one of the first needle holding device and the second needle holding device through the tissue section, passing the needle from the one of the first needle holding device and the second needle holding device to the other of the first needle holding device and the second needle holding device.

In such method, the operating device may comprise a first operating organ, wherein the first operating organ is movable between a normal position and a depressed position, the first operating organ being biased to the normal position by one or more second spring elements with a second biasing force, wherein the operating device is actuated by depression and/or subsequent release of the first operating organ, wherein the first biasing force is smaller than the second biasing force, wherein exerting an actuation force on the first operating organ first results in movement of the first jaw element and the second jaw element towards each other to the take-over position, and subsequently in actuation of the operating device by depression and subsequent release of the first operating organ.

The method may further comprise the step of pulling the needle and attached suture thread through the pierced tissue section after passing the needle from the one to the other of the first needle holding device and the second needle holding device.

In an embodiment, the method may comprise repeating the steps of piercing the needle through the tissue section, and passing the needle between the first and second needle holding device for providing multiple loops of suture threads in the tissue section.

In an embodiment, the method may further comprise that the needle is passed back from the other of the first needle holding device and the second needle holding device to the one of the first needle holding device and the second needle holding device before the needle is again pierced through the tissue section.

In an embodiment, the method may comprise holding the surgical apparatus in a tweezers grip wherein the first operating organ is operated by the index finger or middle finger, and a second operating organ at an opposite side of the suture apparatus is operated by the thumb, or vice versa.

In such tweezers grip a proximal part of the suture apparatus is preferably supported on the web space between the index finger and the thumb and/or a part of the index finger.

In an embodiment, the first holding device and the second holding device are moved over a straight line with respect to each other, when the first jaw element and the second jaw element are moved between the open position and the take-over position.

An embodiment of a surgical suture apparatus according to the invention will now be described in further detail, by way of example only, with reference to the accompanying drawings, in which:

FIG. 7-9 show different positions of the apparatus of FIG. 1 during take-over of a needle between the first and the second holding device.

Figure 1:
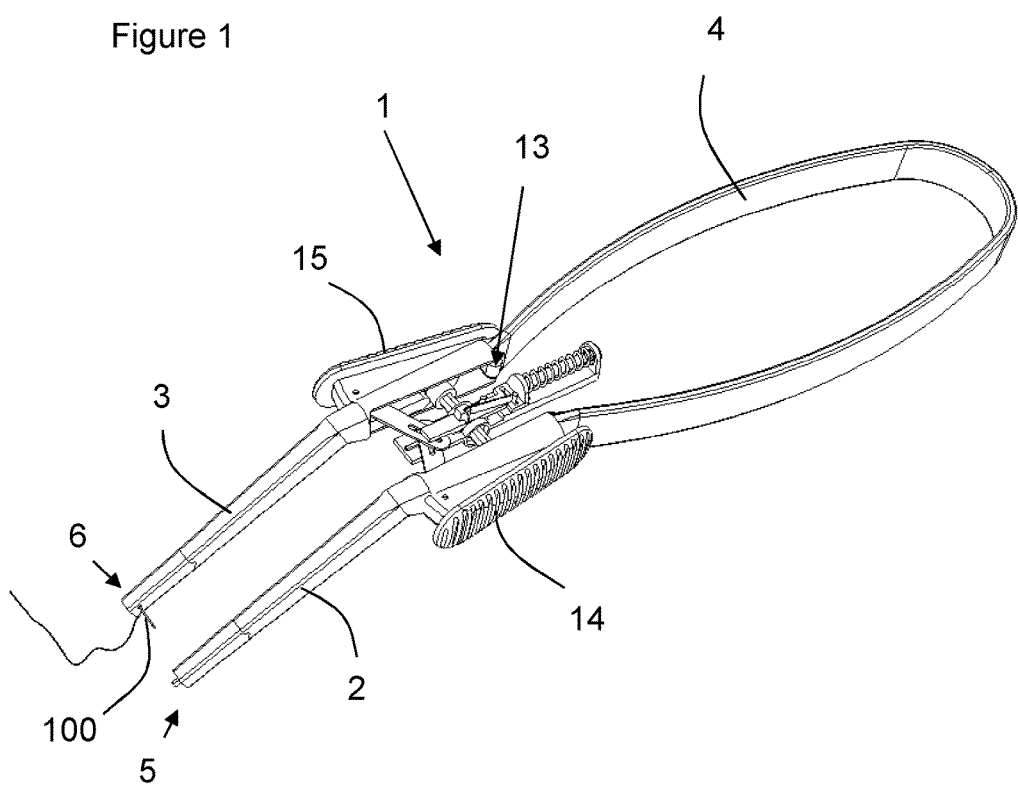
FIG. 1 shows a perspective view of a surgical apparatus according to the invention with a needle.
Figure 2:
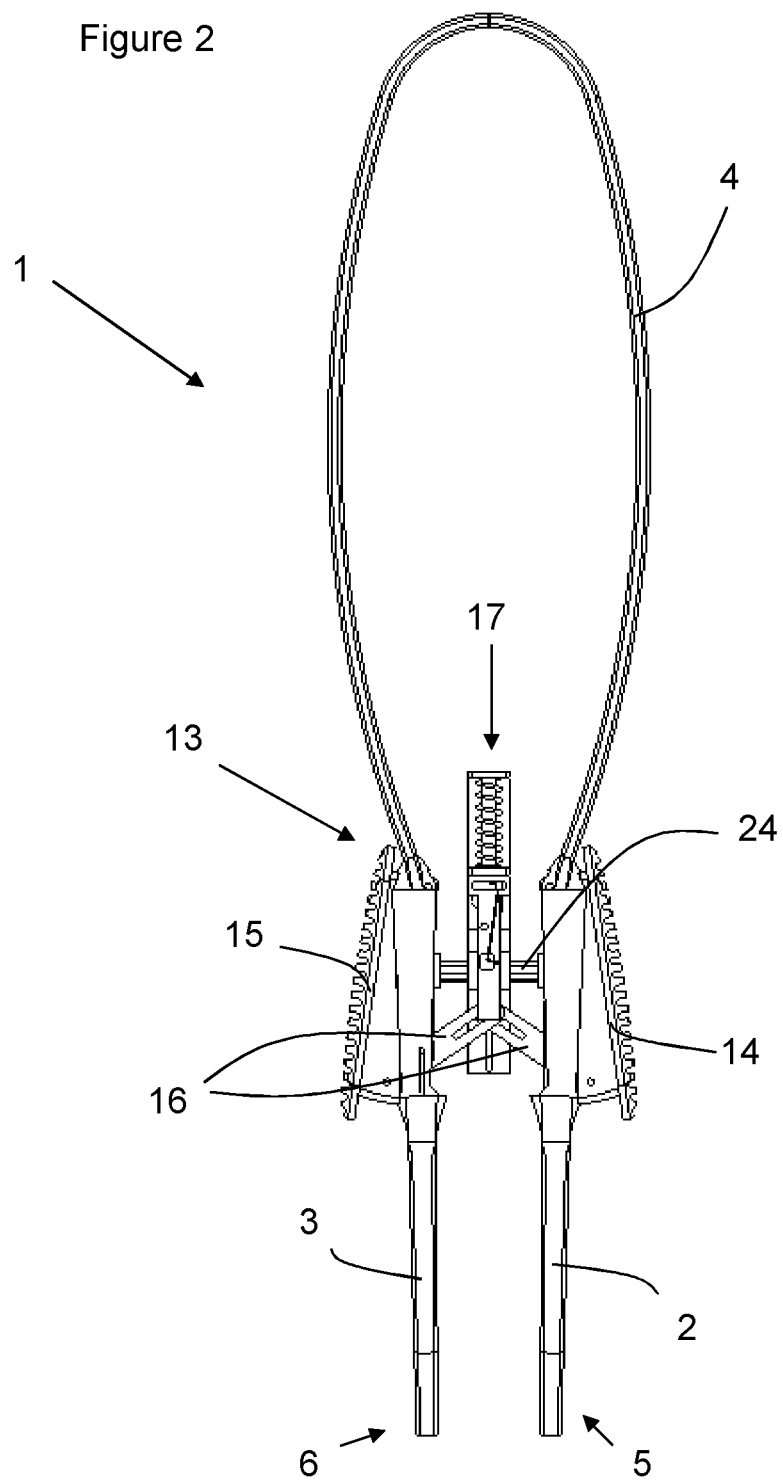
FIG. 2 shows a top view of the surgical apparatus of FIG. 1.

FIGS. 1 and 2 show a perspective view and a top view of a surgical suture apparatus for passing a double-ended surgical needle 100 backwards and forwards. The surgical apparatus is generally denoted by the reference numeral 1.

The surgical apparatus comprises a first jaw element 2 and a second jaw element 3, which are both hooked. The proximal ends of the first jaw element 2 and the second jaw element 3 are connected to each other with an arc-shaped connecting element 4. The connecting element 4 is made of resilient material, for example spring steel, stainless steel or a plastics material, so that the distal ends of the first jaw element 2 and the second jaw element 3 may be moved towards each other. The first jaw element 2, the second jaw element 3 and the connecting element 4 have generally the shape of a pair of tweezers.

In FIGS. 1 and 2, the first jaw element 2 and the second jaw element 3 are shown in an open position. At least partially due to the spring force of the connecting element 4 the first jaw element 2 and the second jaw element 3 are biased to the open position. The first jaw element 2 and the second jaw element 3 may be moved toward each other in a closed position or take-over position. In this closed position, the surgical needle 100 can be passed between the first jaw element 2 and the second jaw element 3 backwards and forwards as now will be described in more detail.

Near the distal end of the first jaw element 2 a first holding device 5 is provided to hold a needle end of the surgical needle 100 and near the distal end of the second jaw element 3 a second holding device 6 is provided to hold an opposed end of the surgical needle 100. The needle 100 is a double-ended needle having a needle groove 101 at both ends for holding and securing the needle 100.

Figure 3:
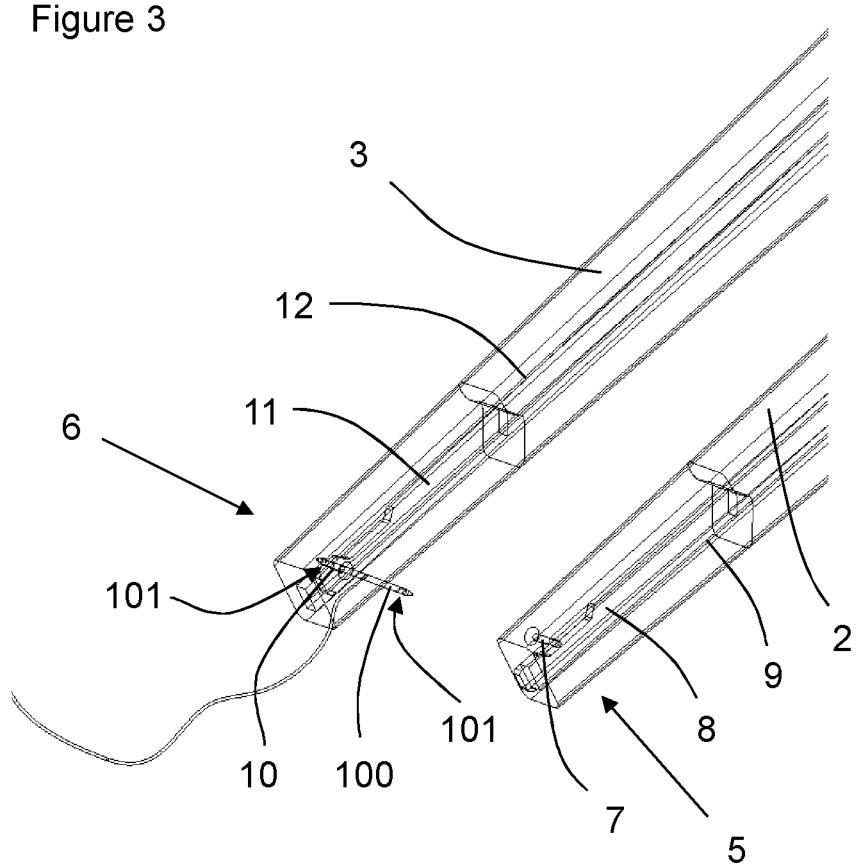
FIG. 3 shows the distal end of the apparatus of FIG. 1 including the first and second holding device in more detail.

The first holding device 5 and the second holding device 6 are shown in more detail in FIG. 3.

The first holding device 5 comprises a first cylindrical recess 7 in the first jaw element 2 to receive a needle end of the needle 100, and a first slidable blade 8 arranged in a guiding channel 9 arranged in the first jaw element 2. The first slidable blade 8 can be moved in a longitudinal direction of the first jaw element 2 between at least a holding position wherein the needle 100 will be held by the first slidable blade 8, and a free position wherein the needle 100 is free to be moved in and out of the first recess 7.

In FIG. 3 the first slidable blade 8 of the first holding device 5 is in the free position. In this free position the first slidable blade 8 is moved to a position where the first slidable blade 8 is not arranged in first recess 7 so that the needle is free to be moved in and out of the first recess 7. When a needle end is positioned in the first recess 7 and the first slidable blade 8 is moved to the holding position, the first slidable blade 8 will be partially arranged in a needle groove 101 of the needle 100, so that the needle end is secured in the first recess 7.

The second holding device 6 comprises a second cylindrical recess 10 in the second jaw element 3 to receive the opposite needle end of the needle 100, and a second slidable blade 11 arranged in a guiding channel 12 in the second jaw element 3. The second slidable blade 11 can be moved in a longitudinal direction of the second jaw element 3 between at least a holding position wherein the needle 100 will be held by the second slidable blade 11 and a free position wherein the needle 100 is free to be moved in and out of the second recess 10.

In FIG. 3, the second slidable blade 11 is positioned in the holding position where the second slidable blade 11 is arranged in a needle groove 101 of the needle 100, so that the needle end is secured in the second recess 10. When the second slidable blade 11 is moved to the free position, the second slidable blade 11 will be no longer be positioned in the needle groove 101 of the needle 100 so that the needle is free to be moved out of the second recess 10.

An operating device 13 is provided to operate the first holding device 5 and the second holding device 6 to alternately hold the needle 100 by its respective needle end. The operating device 13 is shown in more detail in FIG. 4.

The operating device 13 comprises a first operating button 14 arranged on the first jaw element 2 and a second operating button 15 arranged on the second jaw element 3. The first operating button 14 and the second operating button 15 are pivotably mounted on the first jaw element 2 and the second jaw element 3, respectively, and are movable between a normal position, as shown in FIGS. 1 and 2 and a depressed position, wherein the first operating button 14 and the second operating button 15 are pivoted towards the respective jaw element 2, 3.

The first operating button 14 and the second operating button 15 are arranged at opposite sides of the surgical apparatus so that the first operating button 14 and the second operating button 15 can simultaneously be actuated to move the operating buttons 14, 15 from the normal position to the depressed position.

Two articulated arms 16 are each connected with one end to the first and second operating buttons 14, 15 and with the other end to an operating mechanism 17 arranged between the first jaw element 2 and the second jaw element 3. The operating mechanism 17 is a two position switch mechanism, that can be arranged in a first operating position, wherein the first holding device 5 will hold the first needle end, while the second needle end may be moved freely in and out of the second holding device 6, and a second operating position, wherein the second holding device 6 will hold the second needle end, while the first needle end may be moved freely in and out of the first holding device 5, and wherein depression and/or subsequent release of the operating buttons 14, 15 results in a position change from the first operating position to the second operating position or from the second operating position to the first operating position.

Figure 5:
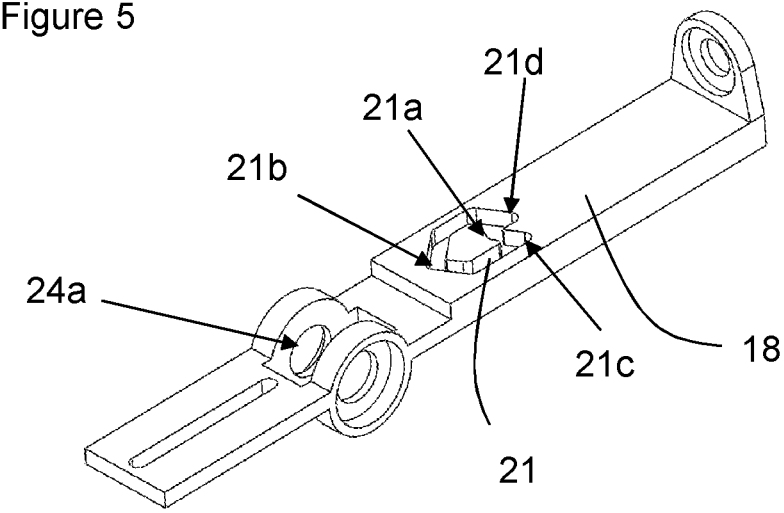
FIGS. 5 and 6 show separately the first and the second operating mechanism members of the operating device of FIG. 4, respectively.
Figure 6:
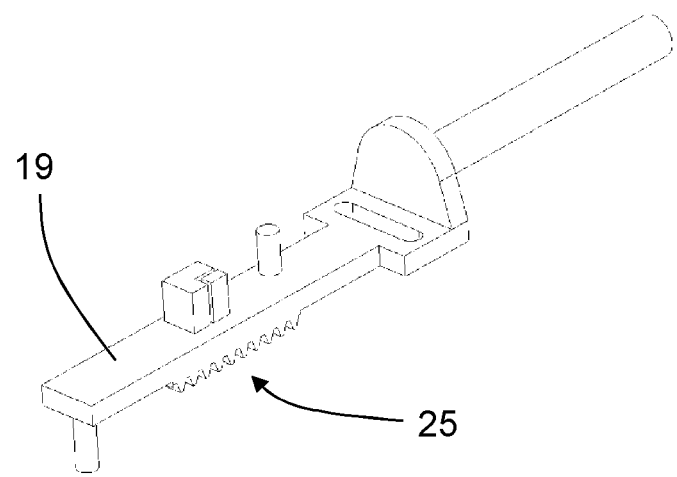

The operating mechanism 17 comprises a first operating member 18 and a second operating member 19, which are separately shown in FIGS. 5 and 6.

The first operating mechanism member 18 and the second operating mechanism member 19 are movable with respect to each other to form the two-position mechanism. The second operating mechanism member 19 is biased by a spring 20 towards the distal end of the apparatus 1.

The first operating mechanism member 18 comprises a continuous groove 21. A pin 22 connected to a leaf spring 23 which leaf spring 23 is mounted on the second operating mechanism member 19 extends into the groove 21, so that movement of the second operating mechanism member 19 with respect to the first operating mechanism member 18 will result in a movement of the pin through the groove 21. Due to the shape of the groove 21 and the biasing force of the spring 20, the pin 22 will, when no actuation force is exerted on the second operating mechanism member 19, be pushed in one of the locations 21a or 21b indicated in FIG. 5.

By moving the first operating button 14 and the second operating button 15 from the normal position to the depressed position, the articulated arms 16 which are mechanically linked to the second operating mechanism member 19 will move the second operating mechanism member 19 with respect to the first operating mechanism member 18 and against the spring force of the spring 20. When the first operating button 14 and the second operating button 15 are released, the spring 20 will push the second operating mechanism member 19 back until the pin 22 comes into one of the locations 21a or 21b.

Due to the shape of the groove 21 in combination with the effect of the leaf spring 23, the pin 22 will upon depression and subsequent release of the first operating button 14 and the second operating button 15 move clockwise through the groove 21 from location 21a to location 21b or from location 21b to location 21a.

As a result, the locations 21a and 21b define the two operating positions of the operating mechanism 17. In these two operating positions the relative position of the first operating mechanism member 18 and the second operating mechanism member 19 is different. This difference in mutual position of the first operating mechanism member 18 and the second operating mechanism member 19 is used to actuate the first holding device 5 and the second holding device 6.

To this end the operating mechanism 17 comprises a rotatable shaft 24 rotatably mounted in a bearing 24a of the first operating mechanism member 18. The rotatable shaft 24 comprises a gear wheel (not shown) which is in gear coupling with a gear rack 25 on the second operating mechanism member 19.

On the shaft 24 a first eccentric cam 26 and a second eccentric cam 27 are arranged. A first cam follower 28 and a second cam follower 29 are provided to cooperate with the first eccentric cam 26 and the second eccentric cam 27, respectively.

The first cam follower 28 is connected to the first slidable blade 8 of the first holding device 5 and the second cam follower 29 is connected to the second slidable blade 11 of the second holding device 6. The first cam follower 28 and the second cam follower 29 are pressed against the respective cam 26, 27 by springs 30 arranged between the first cam follower 28 and the first jaw element 2 and between the second cam follower 29 and the second jaw element 3.

It is remarked that the first eccentric cam 26 and the second eccentric cam 27 are slidably arranged on the shaft 24 to make relative movement of the first jaw element 2 and the second jaw element 3 between the open position and the take-over position possible. However, the first cam 26 and the second cam 27 are rotatably fixed to the shaft 24 so that the cams 26, 27 follow the rotation of the shaft 24. Springs (not shown) may be provided to push the first cam 26 and the second cam 27 towards the respective jaw elements 2, 3 and operating buttons 14, 15. Thus, the spring force of these springs may have an effect on the position of the jaw elements 2, 3 and the position of the operating buttons 14, 15.

In the non-actuated position of the operating mechanism the pin 22 will be arranged in one of the locations 21a and 21b. The respective location of the pin 22 corresponds to a mutual position of the second operating mechanism member 19 with respect to the first operating mechanism member 18, and, as a result, with one of two predetermined rotational positions of the first cam 26 and the second cam 27 with respect to the first cam follower 28 and the second cam follower 29, respectively.

Figure 4:
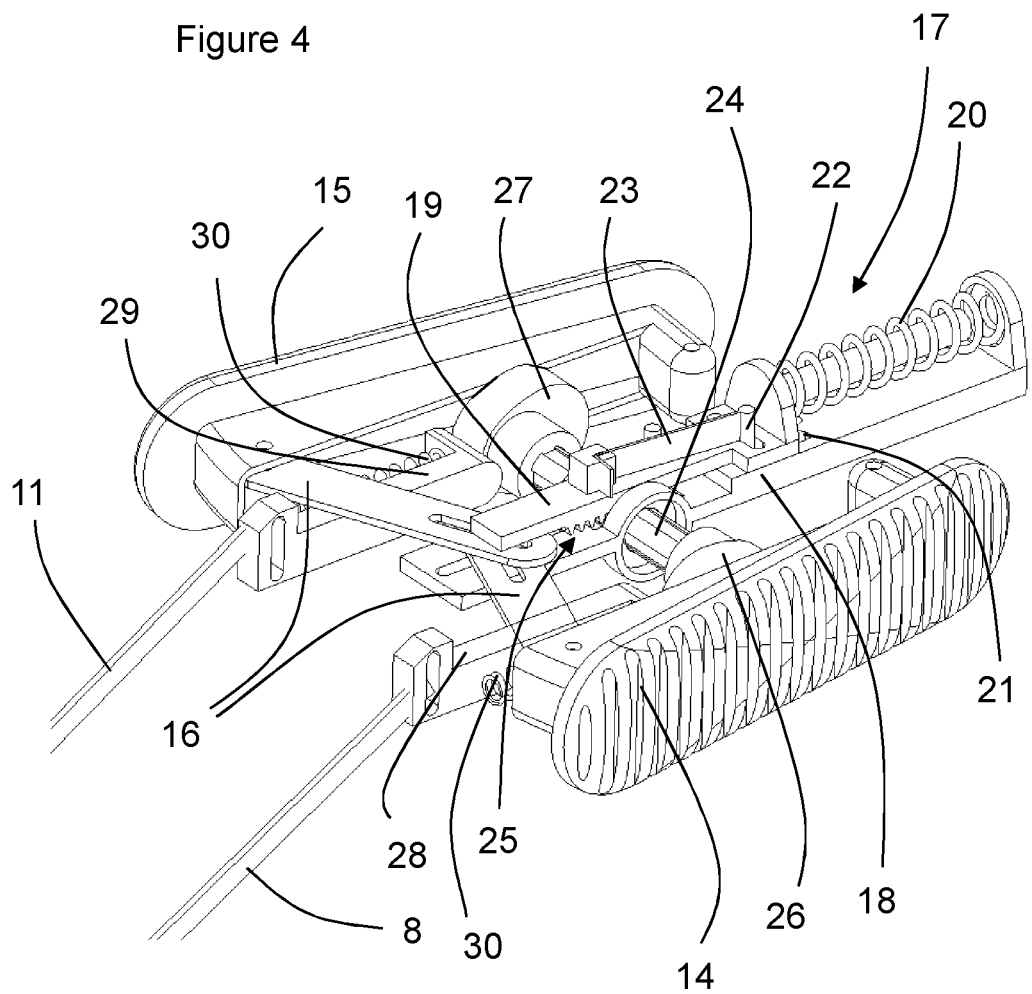
FIG. 4 shows the operating device of the apparatus of FIG. 1.

In the position shown in FIGS. 2 and 4, a large radius of the first cam 26 is positioned in line with the first cam follower 28 to position the first slidable blade 8 in a distal position with respect to the first jaw element 2. In this position the first slidable blade 8 is not positioned in the first recess 7, and thus a needle 100 can freely be moved in and out of the first recess. In contrast, a small radius of the second cam 27 is aligned with the second cam follower 29 so that the second slidable blade 11 is in a proximal position with respect to the second jaw element 3. In this position the second slidable blade 11 is partly positioned within the second recess 10 so that a needle arranged in the second recess 10 is securely held in this second recess 10.

When the operating device 13 is actuated by depression and subsequent release of the first operating button 14 and the second operating button 15, the operating mechanism 17 will change from the first operating position to the second operating position, i.e. the location of the pin 22 will change from location 21a to 21b or vice versa and as a result of the change in the relative position between the first operating mechanism member 18 and the second operating mechanism member 19, the shaft 24 will be rotated over an angle of approximately 180 degrees.

In this second operating position, a small radius of the first cam 26 will be positioned in line with the first cam follower 28 to position the first slidable blade 8 in a proximal position with respect to the first jaw element 2. In this position the first slidable blade 8 is positioned in the first recess 7, and thus the needle 100 is securely held in the first recess 7. And, a large radius of the second cam 27 is aligned with the second cam follower 29 so that the second slidable blade 11 is in a distal position with respect to the second jaw element 3. In this distal position the second slidable blade 11 is not positioned within the second recess 10 so that a needle can be freely moved in and out of the second recess 10.

A following actuation of the operating device 13, i.e. a next depression and release of the first operating button 14 and the second operating button 15 will again result in a subsequent change of the second operating position to the first operating position.

The operating device 13 can be used to pass a needle 100 backwards and forwards between the first holding device 4 and the second holding device 5 when the first jaw element 2 and the second jaw element 3 are arranged in the take-over position, i.e. a relative close position of the first jaw element 2 and the second jaw element 3 wherein the opposite needle ends of a surgical needle 100 are arranged in both the first recess 7 and the second recess 10.

FIGS. 7-9 show a number of steps during the use of the surgical apparatus according to the invention. In these Figures the operating mechanism 17 is covered by a housing.

FIG. 7 shows the apparatus 1 in the non-actuated position. The first jaw element 2 and the second jaw element 3 are biased to the open position with a first biasing force and the first operating button 14 and the second operating button 15 are biased to the normal position by a second biasing force. The first biasing force is at the location of the first and second operating button 14, 15 smaller than the second biasing force.

When the user will exert a sufficiently large pinching actuation force AF on the first and second operating button 14, 15, the first jaw element 2 and the second jaw element 3 will move towards each other from the open position to the closed take-over position.

Since the first and second operating buttons 14, 15 are biased to the open position with a larger biasing force than the first biasing force, the first and second operating buttons 14, 15 will not be depressed to the depressed position for actuation of the operating device 13, until the first jaw element 2 and the second jaw element 3 are in the closed position. It is although remarked that in some embodiments, the first and second operating buttons 14, 15 may already be partly depressed before or during the movement of the first and second jaw elements 2, 3 from the open position to the closed position, but not enough to actually operate the operating device 13.

The apparatus 1 is designed to move the first jaw element 2 and the second jaw element 3 in a mainly translating movement with respect to each other, when moved between the open position and the take-over position, or vice versa. The resilient connecting element 24 is designed to enable such mainly translating movement, while the shaft 24 serves as a guiding element to guide the first jaw element 2 and the second jaw element 3 in this mainly translating movement. Due to this mainly translating movement the first holding device 4 and the second holding device 5 move over a straight line A-A with respect to each other between the open position and the take-over position.

The needle 100 is a straight needle, which is advantageously moved over this straight line A-A. Such straight line movement has the advantage that it results in a reliable and predictable movement of the needle. The position of a needle holding device not holding a needle can be used to more accurately predict where the needle 100 will pierce through tissue, even when the free needle point is not visible.

Once the first jaw element 2 and second jaw element 3 are positioned in the closed position, as shown in FIG. 8, the needle is positioned in the first holding device 5 and the second holding device 6. Thus, the operating device 13 may be operated to pass the needle from the first holding device 5 to the second holding device 6, or vice versa.

Since the jaw elements 2, 3 are already in the closed position and cannot be moved further towards each other, the actuation force will now be used to depress the first operating button 14 and the second operating button 15 to the depressed position for actuation of the operating device 13. FIG. 9 shows the apparatus 1, wherein the first jaw element 2 and second jaw element 3 are positioned in the closed position and the first operating button 14 and the second operating button 15 are in the depressed position.

As a result of the depression of the operating buttons 14, 15, the pin 22 is moved through the groove 21 from location 21a to 21c or from location 21b to 21d (FIG. 5). Subsequent release of the first operating button 14 and second operating button 15 will result due to spring 20 in movement from location 21c to 21b or from location 21d to 21a. Thus, the depression and subsequent release of the operating buttons 14, 15, results in a change between the first operating position and the second operating position, or vice versa. As a consequence the needle is held by the other holding device 5, 6.

Further release of the apparatus will result in movement of the first jaw element 2 and second jaw element 3 from the closed position to the open position, but the needle is now held by the opposite holding device.

It will be clear that renewed actuation of the apparatus with a pinching actuation force on the first operating button 14 and the second operating button 15 will result in the same action as described above, but the needle will now be transferred in the opposite direction.

The above described apparatus 1 can comfortably held by one hand of the user, for example between thumb and index finger, while the arc shaped connecting element 4 provides a convenient support against the hand or wrist of the user.

The apparatus 1 can easily be maneuvered in a surgical site, and can when needed be actuated by one hand of the user without moving the position of the hand with respect to the apparatus 1. Furthermore, the apparatus 1 provides a good view on the distal end of the apparatus where the needle 100 and the first holding device 5 and the second holding device 6 are arranged.

The invention claimed is:

1. A surgical suture apparatus for passing a double-ended surgical needle backwards and forwards, the surgical apparatus comprising:
   a first jaw element and a second jaw element, wherein the first jaw element comprises a first needle holder to hold a first needle end of the surgical needle and the second jaw element comprises a second needle holder to hold a second needle end of the surgical needle, wherein the first jaw element and second jaw element are movable with respect to each other between a take-over position wherein a surgical needle can be passed between the first needle holder and the second needle holder and an open position, wherein the first needle holder and second needle holder are spaced further from each other, wherein the surgical apparatus comprises one or more first spring elements to bias the first jaw element and the second jaw element to the open position with a first biasing force, and
   an operating device to operate the first needle holder and the second needle holder to alternately hold the first needle end by the first needle holder and the second needle end by the second needle holder,
   wherein the operating device comprises a first operating element, wherein the first operating element is movable between a normal position and a depressed position, the first operating element being biased to the normal position by one or more second spring elements with a second biasing force,
   wherein the operating device comprises a second operating element, wherein the second operating element is movable between a normal position and a depressed position, the second operating element being biased to the normal position by the one or more second spring elements and/or by one or more third spring elements with a third biasing force,
   wherein the operating device is actuated by depression and/or subsequent release of the first operating element and the second operating element, when the first jaw element and the second jaw element are moved into the take-over position,
   wherein the first operating element is arranged on the first jaw element and the second operating element is arranged on the second jaw element, and wherein the first operating element and the second operating element are arranged at opposite sides of the surgical apparatus, and
   wherein the first biasing force is smaller than the second biasing force and the first biasing force is smaller than the third biasing force such that simultaneous actuation force on the first operating element and the second operating element first results in movement of the first jaw element and the second jaw element towards each other, and subsequently in actuation of the operating device.

2. The surgical apparatus of claim 1, wherein the first operating element is arranged on the first jaw element at a side faced away from the second jaw element.

3. The surgical apparatus of claim 1, wherein the operating device comprises a two position switch mechanism, that can be arranged in a first operating position, wherein the first needle holder will hold the first needle end, while the second needle end may be moved freely in and out of the second needle holder, and a second operating position, wherein the second needle holder will hold the second needle end, while the first needle end may be moved freely in and out of the first needle holder, and wherein depression and/or subsequent release of the operating element results in a position change from the first operating position to the second operating position or from the second operating position to the first operating position.

4. The surgical apparatus of claim 1, wherein the first needle holder and the second needle holder are arranged at a distal end of the first jaw element and the second jaw element, respectively.

5. The surgical apparatus of claim 1, further comprising a connecting element providing a structural connection between the first jaw element and the second jaw element, wherein the connecting element is an arc shaped resilient element connecting a proximal end of the first jaw element to a proximal end of the second jaw element.

6. The surgical apparatus of claim 5, wherein the one or more first spring elements comprise the connecting element.

7. The surgical apparatus of claim 1, wherein the first needle holder and the second needle holder each comprise an elongated holding element which is movable between a holding position and a free position.

8. The surgical apparatus of claim 1, wherein the first jaw element and the second jaw element each comprise a recess for receiving the first needle end and the second needle end, respectively, wherein the first needle holder and the second needle holder are configured to hold the first needle end or the second needle end in the respective recess.

9. The surgical apparatus of claim 1, wherein the operating device comprises an operating mechanism arranged between the first jaw element and the second jaw element.

10. The surgical apparatus of claim 1, wherein in the open position the first needle holder and the second needle holder are at least a length of the surgical needle spaced from each other.

11. The surgical apparatus of claim 1, wherein the first operating element is a first operating button and/or the second operating element is a second operating button.

12. The surgical apparatus of claim 1, wherein the surgical apparatus is configured to be held and operated by a single hand of a user.

13. The surgical apparatus of claim 1, wherein the first operating element is actuated by an index finger and/or middle finger and the second operating element is actuated by a thumb of a single hand of the user.

14. The surgical apparatus of claim 1, wherein the actuation force is provided as a pinching actuation force of the thumb and a finger of a single hand of the user.

15. The surgical apparatus of claim 14, further comprising a connecting element providing a structural connection between the first jaw element and the second jaw element,
   wherein the connecting element is shaped to be supported, during use, by a web space of the hand between thumb and index finger and/or a part of the index finger.

16. The surgical apparatus of claim 1, wherein the apparatus is designed to move the first needle holder and the second needle holder over a straight line with respect to each other, when the first jaw element and the second jaw element are moved between the open position and the take-over position.

17. The surgical apparatus of claim 16, wherein the surgical apparatus comprises one or more guides for guiding the first and second jaw element in a mainly translating movement, when the first jaw element and the second jaw element are moved with respect to each other between the open position and the take-over position.

18. The surgical apparatus of claim 1, further comprising a connecting element providing a structural connection between the first jaw element and the second jaw element.

\* \* \* \* \*